United States Patent [19]

Fernandez et al.

[11] Patent Number: 5,001,287
[45] Date of Patent: Mar. 19, 1991

[54] PURIFICATION OF SATURATED HALOCARBONS

[75] Inventors: Richard E. Fernandez, Bear; V. N. Mallikarjuna Rao, Wilmington, both of Del.

[73] Assignee: E. I. Du Pont de Nemours and Company, Wilmington, Del.

[21] Appl. No.: 305,442

[22] Filed: Feb. 2, 1989

[51] Int. Cl.$^5$ .............................................. C07C 17/38
[52] U.S. Cl. ..................................... 570/178; 570/117
[58] Field of Search ................................ 570/178, 177

[56] References Cited

U.S. PATENT DOCUMENTS

| | | | |
|---|---|---|---|
| 2,999,885 | 9/1961 | Heberling | 260/648 |
| 3,004,075 | 10/1961 | Marcall | 260/648 |
| 3,218,363 | 11/1965 | Haszeldine | 260/648 |
| 3,317,619 | 5/1967 | Hedge et al. | 570/177 |
| 3,381,041 | 4/1968 | Kometani et al. | 260/653 |
| 3,696,156 | 10/1972 | Weeks | 260/648 F |
| 4,129,603 | 12/1978 | Bell | 260/653 |
| 4,158,675 | 6/1979 | Potter | 260/653.7 |

FOREIGN PATENT DOCUMENTS 160718 2/1984 German Democratic Rep. .
1031409 6/1966 United Kingdom .

OTHER PUBLICATIONS

M. Hudlicky, "Chemistry of Organic Fluorine Compounds", p. 173, 2nd Edition, 1976.
Lacher et al., Trans. Faraday Soc., "The Hydrogenation of Organic Fluorides and Chlorides", 52, pp. 1500–1508 (1956).

*Primary Examiner*—Alan Siegel

[57] ABSTRACT

A process for treating an impure mixture consisting essentially of at least one olefinic impurity and at least one saturated halocarbon selected from fluorocarbons and fluorohydrocarbons by contacting the mixture with a source of hydrogen in the presence of a hydrogenation catalyst, whereby the olefinic impurity is converted to a hydrogenated form thereof, to produce a treated mixture consisting essentially of the hydrogenated form of the olefinic impurity or impurities and the saturated halocarbon or halocarbons from the impure mixture.

20 Claims, No Drawings

PURIFICATION OF SATURATED HALOCARBONS

FIELD OF THE INVENTION

This invention relates to the purification of saturated fluorohalocarbons and/or fluorohalohydrocarbons containing olefinic impurities, and especially to a reductive process for removing olefinic impurities.

BACKGROUND OF THE INVENTION

U.S. Pat. No. 2,999,855 discloses a process for the removal of unsaturated fluorocarbons and saturated fluorohydrocarbons from saturated perfluorocarbon product streams by treatment with aqueous potassium permanganate at 20° to 95° C. GB 1,031,409 discloses a process for the purification of 2,2,2-trifluoro-1-chloro-1-bromoethane ($CF_3CHBrCl$) to remove fluorinated halogen butenes by treatment with an alcoholic solution of an alkali metal hydroxide or alcoholate.

U.S. Pat. No. 3,004,075 discloses a process for purifying impure saturated perfluorocarbon of 2-6 carbon atoms in which the impurities consist essentially of unsaturated highly fluorinated compounds which may also contain chlorine or hydrogen, which comprises intimately contacting the impure saturated perfluorocarbon with at least one member of the group consisting of piperdine, pyrrolidine and pyridine and mixtures thereof, at a temperature from about 0° to about 80° C, and separating the purified saturated perfluorocarbon from the reaction mixture.

U.S. Pat. No. 3,218,363 discloses a method of purifying a saturated perhalocarbon in which the halogen substituents are selected from the group consisting of fluorine and chlorine, said perhalocarbon containing impurities selected from the group consisting of (1) hydrogen-containing compounds of structure R-H wherein R is selected from the group consisting of perfluorocarbons, perfluorochlorocarbons, polyfluorohydrocarbons and polyfluorochlorohydro-carbons; comprising subjecting such perhalocarbon to an energy source consisting essentially of non-radiant heat at a temperature in the range of from 350° to 700° C in the presence of $O_2$ and an initiator selected from the group consisting of $F_2$, $Cl_2$, $Br_2$ and interhalogen compounds, for a time sufficient to oxidize the major part of the impurities, to form products easily removable from said perhalocarbon, but insufficient to cause degradation of a significant amount of said perhalocarbon.

U.S. Pat. No. 3,381,041 discloses a process for purifying impure 1-9 carbon fluorinated alkanes consisting of carbon and fluorine, and fluorinated alkanes consisting of carbon, fluorine and at least one member of the group consisting of hydrogen, chlorine, bromine and iodine to remove halogenated alkenes, which comprises contacting an impure fluorinated compound, at about 0° to 150° C for about 10 seconds to 30 minutes, with a mixture of $H_2SO_4$ of at least 50 percent by weight concentration, and at least one mercury material, in the order of from 0.1 to 20 percent by weight of the sulfuric acid content of said mixture.

U.S. Pat. No. 3,696,156 discloses a process for the purification of 2-6 carbon saturated fluoroperhalohydro-carbons, containing only fluorine or fluorine and chlorine, and contaminated with perfluoro- and perfluorochloro-olefins, by vapor phase contact at 180-250° C. with alumina containing $\geqq 0.1\%$ by weight base selected from alkali(ne earth) metal (hydr)oxides.

U.S. Pat. No. 4,129,603 discloses a process for reducing the 1,1-difluoro-2-chloroethylene, $CF_2=CHCl$, by-product obtained from the reaction of 1,1,1-trihalo-2-chloroethane and HF to produce 1,1,1,2-tetrafluoroethane, $CF_3CH_2F$, by contacting the reaction products with a metal permanganate in a liquid medium.

U.S. Pat. No. 4,158,675 teaches the removal of 1,1difluoro-2-chloroethylene from the 1,1,1,2-tetrafluoroethane product stream produced as in U.S. Pat. No. '603 above by vapor phase hydrofluorination of a 1,1,1-trihalo-2-chloroethane, by passing the impure stream together with HF over a chromium oxide catalyst at lower temperatures (100-275° C.) than the hydrofluorination temperatures (300-400° C.) of the tetrafluoroethane production step.

East German Patent 160,718 discloses a process for the separation and purification of perfluorinated alkanes from mixtures containing perfluoroolefins and HF which comprises quantitative reaction of olefinic impurities to form water soluble products by their reaction with reactive nucleophiles in the presence of acid acceptors, or reaction with alkali salts of reactive nucleophiles, or reaction with aqueous alkali solutions. The perfluorinated alkanes form a distinct phase which is separated and then refined.

The olefinic impurities which are present as impurities in the manufacture of saturated fluorocarbons and fluorohydrocarbons are particularly undesirable as contaminants as they may be toxic and for most uses their concentrations in the saturated products must be lowered to as a low a level as is practically possible. This is particularly true because the fluorocarbons and fluorohydrocarbons can be widely used as solvents, cleaning agents, blowing agents, and refrigerants where toxicity must be substantially eliminated. Distillation and other conventional physical methods which may be used to lower the concentrations of olefinic impurities are generally ineffective when the boiling points are too close and are generally too costly. Therefore, various chemical treatments have been proposed, some of which are described above. None of these prior processes is entirely satisfactory from a commercial viewpoint. The aqueous alkaline metal permanganate treatments of the U.S. Pat. Nos. '855 and '603, for example, require that the halocarbon products exiting the treatment medium be dried (separated from its entrained water) before further refining, which adds to the expense of the treatment. Moreover, where saturated halo-hydrocarbon products are being treated, the possibility exists that some of the valuable saturated material could be lost to the alkaline oxidative medium along with the unsaturated impurities. The high temperatures of the U.S. Pat. Nos. '156 and '675 are objectionable because of the increased cost of unsaturates removal. Further the U.S. Pat. No. '156 treatment appears limited to perhalocarbons since hydrogen-bearing halocarbons are possibly susceptible to dehydrohalogenation to form unsaturated products under the high temperature alkaline process of the disclosed process.

It is an object of this invention to provide a hydrogenation process for reducing the concentration of olefinic impurities in fluorocarbons and fluorohydrocarbons, in particular in such fluorocarbons and fluorohydrocarbons having 2 to 4 carbon atoms.

Another object is to provide a process as above that operates at relatively low temperatures.

Still another object is to provide a process as above that reduces the content of the olefinic impurity in the fluorocarbon and fluorohydrocarbon process streams without substantial yield loss of the hydrogen-bearing halocarbon components.

Yet another object is to provide a process as above where the hydrogenated olefinic impurity can be recovered by distillation and used as a separate product.

A further object is to provide a process for which no drying is required.

SUMMARY OF THE INVENTION

This invention provides for a process for treating an impure mixture consisting essentially of at least one olefinic impurity and at least one saturated halocarbon selected from fluorocarbons and fluorohydrocarbons by contacting the mixture with a source of hydrogen in the presence of a hydrogenation catalyst, whereby the olefinic impurity is converted to a hydrogenated form thereof, to produce a treated mixture consisting essentially of the hydrogenated form of the olefinic impurity or impurities and the saturated halocarbon or halocarbons from the impure mixture. If desired or if necessary, the hydrogenated form of the olefinic impurity can be separated from the treated mixture by conventional means to produce a fluorocarbon and/or fluoro-hydrocarbon substantially free of olefinic impurity or the hydrogenated form of the olefinic impurity. In addition, if the hydrogenated form of the olefinic impurity is itself useful, it may be recovered as product.

Such treatment enables the recovery of the saturated fluorocarbons and/or fluorohydrocarbons directly and substantially free of olefinic impurities and without significant yield loss. It also enables the recovery of the fluorocarbons and/or fluorohydrocarbons not only substantially free of olefinic impurities but also substantially free of water without the need for an additional drying step.

DETAILS OF THE INVENTION

The invention process is conducted by contacting, either batchwise or continuously, a substantially dry impure mixture consisting essentially of olefinic impurity(ies), saturated fluorocarbon(s) and/or fluorohydrocarbon(s) in gaseous or liquid form with a hydrogenation catalyst, e.g. Pd/C, Pt/C, Rh/C and Re/C. It is preferably conducted as a continuous process wherein a gaseous stream of impure mixture is passed through a particulate solid bed of the hydrogenation catalyst, maintained at the desired temperature by heating, if necessary. The exit stream, i.e. treated mixture, from the reactor with the saturated fluorocarbon(s) and/or fluorohydrocarbon(s) substantially free of olefinic impurities can be treated, if desired, by conventional means for separating the saturated fluorocarbons and/or fluorohydrocarbons from the hydrogenated olefinic impurities.

The invention may be applied to the purification of saturated fluorocarbons and fluorohydrocarbons and mixtures thereof, whatever their source, that contain one or more fluorine atoms in the molecule and are contaminated with olefinic impurities. Included are perfluoro- and fluorohydrocarbons composed of: carbon and fluorine and carbon, hydrogen and fluorine. The saturated fluorocarbons and/or fluorohydrocarbons preferably contain 2 to 4 carbon atoms, more preferably 2 to 3, most preferably 2 because of their greater commercial importance.

The saturated fluorocarbons and/or fluorohydro-carbons include cyclic as well as acyclic compounds represented by the empirical formula $C_nH_mF_p$, where n is an integer from 2 to 4, m is an integer from 0 to 9, and p is an integer from 1 to 10, provided that m +p equals 2n +2 when the compound is acyclic and equals 2n when the compound is cyclic.

In one embodiment the fluorocarbons are fluoroalkanes, i.e. acyclic, represented by the above empirical formula where n is 2 or 3, m is 0 to 7 and p is 1 to 8.

In another embodiment the fluorohydrocarbons are acyclic hydrogen-bearing alkanes, where n is 2, m is 1 to 5, p is 1 to 5, and m +p is 6.

In still another embodiment the compounds to be treated are fluorinated hydrogen-bearing alkanes where n is 3, m is 1 to 7, p is 1 to 7, and m +p is 8.

Representative saturated halocarbons that can be treated in accordance with the method of the invention when contaminated with olefinic impurities include fluorocarbons such as $CF_3CF_3$, $CF_3CF_2CF_3$, $CF_3CF_2CF_2CF_3$, and cyclo-$C_4F_8$; and fluorohydrocarbons such as $CHF_2CF_3$, $CHF_2CHF_2$, $CF_3CH_2F$, $CF_3CH_3$, $CHF_2CH_3$, $CH_2FCH_3$, $CF_3CF_2CHF_2$, $CF_3CF_2CH_3$, $CH_3CHFCH_3$, $CH_3CH_2CH_2F$, and $(CF_3)_2CHCF_3$.

The invention process is capable of removing a wide variety of carbon-carbon unsaturated compounds when present in the impure mixture, notably $C_2$ to $C_4$ olefins composed of carbon and hydrogen and optionally bearing halogen substituents, generally fluorine, chlorine and/or bromine and boiling over a wide range. The invention process is particularly effective for the removal of the $C_2$ olefinics, the most commonly occurring of the olefinic impurities in the fluorocarbons and fluorohydrocarbons described above.

Representative olefinic impurities that can be removed from the saturated fluorocarbons and fluorohydro-carbons include hydrocarbon and halocarbon olefins including cis and trans isomers thereof, such as: $CH_2=CH_2$, $CH_2=CHCl$, $CHCl=CHCl$, $CH_2=CCl_2$, $CHCl=CCl_2$, $CF_2=CH_2$, $CF_2=CF_2$, $CF_2=CHF$, $CF_2=CClF$, $CH_2=CClF$, $CH_3CF=CH_2$, $CF_3CF=CF_2$, $CF_3CH=CHCF_3$, $(CF_3)_2C=CF_2$, and $CClF_2CF_2CF=CF_2$.

Since most of the olefinic impurity content of the saturated fluorocarbons and fluorohydrocarbons is usually removable at reasonable cost by standard physical methods such as fractional distillation, the quantity of the olefinic impurities remaining to be treated by the method of this invention will generally be less than about 1% by weight, and more usually will lie in the range of about 0.5% down to about 0.001% by weight of the saturated halocarbon, or about 5000 ppm down to about 10 ppm. The invention process has been found to be effective to lower the unsaturated content to below 10 ppm and in most cases to below the gas chromatographic detection limit.

The invention process is especially applicable to the purification of saturated fluorocarbons and fluorohydrocarbon products obtained by reaction of HF with a chlorine- or bromine-containing precursor of the products. Included, for example, is $CH_3CF_3$ contaminated with vinylidene chloride, $CH_2=CCl_2$, obtained by hydrofluorination of methylchloroform in the presence or absence of catalyst; $CF_3CH_2F$ obtained by catalytic reaction of HF, $CX_3CH_2Cl$ or $CX_2=CHCl$, where X =Cl or F, and containing 1,1-difluoro-2-chloroethylene, $CF_2=CHCl$, as impurity. All these reactions, the conditions employed and the compositions of the product streams produced thereby are well known in the prior art.

The impure mixture consisting essentially of saturated fluorocarbons and/or fluorohydrocarbons and olefinic impurities is contacted with hydrogen in the presence of a hydrogenation catalyst containing a Group VIII metal or rhenium, supported or unsupported, with Pd/C being preferred, at about 50° to about 300° C, and more preferably 50° to about 200° C in any suitable reactor, including fixed and fluidized bed reactors.

The contact time under the conditions of this invention should be sufficient to allow hydrogenation of the olefinic impurity without substantially affecting the saturated halocarbon. Contact time can vary widely, but, generally, will be about 5 to 100 seconds, preferably about 10 to 30 seconds.

The molar ratio of hydrogen to the saturated fluorocarbons and/or fluorohydrocarbons can vary widely, but generally ranges from about 0.1 to 2, preferably about .5 to 1.5, and more preferably about 0.5 to 1.0.

Hydrogen can be fed either in the pure state or diluted with an inert gas, e.g., nitrogen, helium or argon.

While vapor phase reactions are preferred, the hydrogenation reactions may also be done in the liquid phase.

The hydrogenated form of the olefinic impurities can be separated and recovered by conventional means such as distillation.

Pressure is not critical. Atmospheric and superatmospheric pressures are the most convenient and are therefore preferred.

EXAMPLES

In the following illustrative examples of the invention, parts and percentages are by weight and temperatures are in degrees Celsius unless otherwise specified. All pertinent compositions are given in area percent. The reactor effluent was sampled on-line with a Hewlett Packard HP 5890 gas chromatograph using a 20 foot long, one-eighth inch diameter, column containing Krytox° perfluorinated polyether on an inert support and a helium flow of 35 cc/min. Gas chromatographic conditions were 70° C. for three minutes followed by temperature programming to 180° C. at a rate of 6° C./minute.

EXAMPLES 1-4

A 3/8" dia. stainless steel U-tube of 15 mL capacity was charged with 0.5% Pd/C (6.65 g, 4/8 mesh) and impure 1,1,1,2-tetrafluoroethane (HFC-134a) containing ppm $CHCl=CF_2$ (FC-1122) was passed over the catalyst, together with hydrogen, at 150° C. The flow rates of $H_2$ (cc/min) and the impure HFC-134a (mL/hr) together with the hydrogenation results are shown in Table 1. The products exiting the reactor were analyzed by gas chromatography and found to contain less than 10 ppm FC-1122, which is the gas chromatograph detection limit, in three of the four examples, and 10 ppm FC-1122 in the fourth. Additionally, HFC-134a was recovered substantially unchanged by this treatment.

TABLE 1

| EX. | Run Time | H$_2$ Flow | HFC-134a Flow | % HFC-134a | FC-1122 (ppm) | HFC-142[1] (ppm) |
|---|---|---|---|---|---|---|
| 1 | 8.2 h | 10 | 5 | 99.6 | <10 | ND[2] |
| 2 | 16.7 | 10 | 5 | 99.6 | <10 | 350 |
| 3 | 20.7 | 10 | 10 | 99.6 | 10 | 330 |
| 4 | 23.2 | 10 | 20 | 99.6 | <10 | 240 |

[1]HFC-142 = $CH_2ClCHF_2$
[2]non-detectable, <10 ppm

WHAT IS CLAIMED:

1. A process for treating an impure mixture consisting essentially of at least one olefinic impurity and at least one saturated halocarbon selected from fluorocarbons and fluorohydrocarbons by contacting the mixture with a source of hydrogen in the presence of a hydrogenation catalyst, whereby the olefinic impurity is converted to a hydrogenated form thereof, to produce a treated mixture- consisting essentially of the hydrogenated form of the olefinic impurity or impurities and the saturated halocarbon or halocarbons from the impure mixture.

2. The process according to claim 1 wherein the contacting is conducted at a temperature from about 50° C. to about 300° C.

3. The process according to claim 1 wherein the contacting is conducted at a temperature from about 50° C. to about 200° C.

4. The process according to claim 1 wherein the hydrogenation catalyst comprises at least one metal selected from Group VIII metals and rhenium.

5. The process according to claim 4 wherein the hydrogenation catalyst is supported on carbon.

6. The process according to claim 1 wherein the treated mixture is subjected to fractional distillation to separate the components thereof.

7. The process according to claim 1 wherein the saturated halocarbon contains from 2 to 4 carbon atoms.

8. The process according to claim 7 wherein the saturated halocarbon is selected from at least one of $CF_3CF_3$, $CF_3CF_2CF_3$, $CF_3CF_2CF_2CF_3$, cyclo-$C_4F_8$, $CHF_2CF_3$, $CHF_2CHF_2$, $CF_3CH_2F$, $CF_3CH_3$, $CHF_2CH_3$, $CH_2FCH_3$, $CF_3CF_2CHF_2$, $CF_3CF_2CH_3$, $CH_3CHFCH_3$, $CH_3CH_2CH_2F$, and $(CF_3)_2CHCF_3$.

9. The process according to claim 1 wherein the olefinic impurity contains from 2 to 4 carbon atoms.

10. The process according to claim 9 wherein the olefinic impurity is at least one selected from $CH_2=CH_2$, $CH_2=CHCl$, $CHCl=CHCl$, $CH_2=CCl_2$, $CHCl=CCl_2$, $CF_2=CH_2$, $CF_2=CF_2$, $CF_2=CHF$, $CF_2=CClF$, $CH_2=CClF$,
    $CF_3$, $(CF_3)_2C=CF_2$, and $CH_3CF=CH_2$, $CF_3CF=CF_2$, $CF_3CH=CH$ $CClF_2CF_2CF=CFz$.

11. The process according to claim 1 wherein the amount of olefinic impurity in the impure mixture is less than 1% by weight.

12. The process according to claim 11 wherein the molar ratio of hydrogen to the saturated halocarbons is from about 0.1:1 to about 2:1.

13. The process according to claim 12 wherein the impure mixture is passed together with hydrogen over a Pd/C catalyst; wherein the contacting is conducted at a temperature from about 50° C. to about 300° C; wherein the saturated halocarbons contain from 2 to 4 carbon atoms; and wherein the olefinic impurities contain from 2 to 4 carbon atoms.

14. The process according to claim 1 wherein the impure mixture is passed together with hydrogen over a Pd/C catalyst.

15. The process according to claim 14 wherein the contacting is conducted at a temperature from about 50° C. to about 300° C.

16. The process according to claim 15 wherein the contact time is from about 5 to 100 seconds.

17. The process according to claim 16 wherein the molar ratio of hydrogen to the saturated halocarbons is from about 0.1:1 to about 2:1.

18. The process according to claim 17 wherein the saturated halocarbons contain 2 carbon atoms; and wherein the olefinic impurities are $C_2$ olefins.

19. The process of claim 18 wherein the amount of olefinic impurity in the impure mixture is less than 1% by weight.

20. The process of claim 1 wherein the hydrogenation catalyst comprises at least one metal selected from Group VIII metals and rhenium; wherein the molar ratio of hydrogen to the saturated halocarbons is from about 0.1:1 to about 2:1; wherein the saturated halocarbons contain from 2 to 4 carbon atoms; wherein the olefinic impurities comprise $C_2$ olefins; and wherein the amount of olefinic impurity in the impure mixture is less than 1% by weight.

* * * * *

UNITED STATES PATENT AND TRADEMARK OFFICE
CERTIFICATE OF CORRECTION

PATENT NO. : 5,001,287                                    Page 1 of 2
DATED     : March 19, 1991
INVENTOR(S) : Richard E. Fernandez, V. N. Mallikarjuna Rao It is certified that error appears in the above-identified patent and that said Letters Patent is hereby corrected as shown below:

At Col. 4, line 41, "$CH_2= CC_{12}$" should read -- $CH_2= CCl_2$ --.

At Col. 5, line 44 "tox°" should read -- tox® --.

At Col. 6, line 19 "ture-" should read -- ture --.

At Col. 6, line 24 "C. to" should read -- C to --.

At Col. 6, line 27 "C. to" should read -- C to --.

At Col. 6, line 41 "$CHF2^{CHF}2$" should read -- $CHF_2CHF_2$ --.

At Col. 6, line 48 "$CH_2= CC_{12}$" should read -- $CH_2= CCl_2$ --.

At Col. 6, line 49 "$CHCl= CC_{12}$" should read -- $CHCl= CCl_2$ --.

At Col. 6, lines 51 and 52 "$CF_3$, $(CF_3)_2C=CF_2$, and $CH_3CF=CH_2$, $CF_3CF=CF_2$, $CF_3CH=CH$ $CClF_2CF_2CF=CF_z$" should read -- $CH_3CF=CH_2$, $CF_3CF=CF_2$, $CF_3CH=CHCF_3$, $(CF_3)_2C=CF_2$, and $CClF_2CF_2CF=CF_2$ --.

UNITED STATES PATENT AND TRADEMARK OFFICE
CERTIFICATE OF CORRECTION

PATENT NO. : 5,001,287

DATED : March 19, 1991

INVENTOR(S) : Richard E. Fernandez, et al

It is certified that error appears in the above-identified patent and that said Letters Patent is hereby corrected as shown below:

At Col. 6, line 62 "C. to" should read -- C to --.

At Col. 7, line 3 "50$_®$CC." should read -- 50°C --.

Signed and Sealed this

Twenty-second Day of September, 1992

Attest:

DOUGLAS B. COMER

Attesting Officer     Acting Commissioner of Patents and Trademarks